US008846384B2

(12) United States Patent
Gerritse et al.

(10) Patent No.: US 8,846,384 B2
(45) Date of Patent: Sep. 30, 2014

(54) SYSTEM FOR DETECTING MICROBIAL CONTAMINATION (75) Inventors: Jan Gerritse, Apeldoorn (NL); Johannes Wouterus van Groenestijn, Apeldoorn (NL); Neeltje Dina Zegers, Delft (NL)

(73) Assignee: Nederlandse Organisatie voor toegepast-natuurwetenschappelijk onderzoek TNO, Delft (NL)

( * ) Notice: Subject to any disclaimer, the term of this patent is extended or adjusted under 35 U.S.C. 154(b) by 768 days.

(21) Appl. No.: 12/744,215

(22) PCT Filed: Nov. 24, 2008

(86) PCT No.: PCT/NL2008/050741
§ 371 (c)(1),
(2), (4) Date: Oct. 28, 2010

(87) PCT Pub. No.: WO2009/067011
PCT Pub. Date: May 28, 2009

(65) Prior Publication Data
US 2011/0033881 A1    Feb. 10, 2011

(30) Foreign Application Priority Data

Nov. 23, 2007 (EP) .................................... 07121431
Feb. 27, 2008 (EP) .................................... 08152030

(51) Int. Cl.
*C12M 1/00*    (2006.01)
*C12M 3/00*    (2006.01)
*C12Q 1/04*    (2006.01)
*C12Q 1/54*    (2006.01)

(52) U.S. Cl.
CPC ............ *C12Q 1/04* (2013.01); *G01N 2333/924* (2013.01); *G01N 2333/245* (2013.01); *C12Q 1/54* (2013.01)
USPC ........... 435/308.1; 435/30; 422/527; 422/534

(58) Field of Classification Search
CPC ...... C12Q 1/04; C12Q 1/54; G01N 2333/245; G01N 2333/924; B01N 21/253; B01N 21/6428; B01N 21/6452; B01L 3/502; B01L 2300/0681; B01L 2300/0877; B01L 2400/0487; C12M 33/06
USPC .............. 422/527, 534, 535, 566; 435/18, 30, 435/288.7, 308.1
See application file for complete search history.

(56) References Cited

U.S. PATENT DOCUMENTS 3,283,485 A * 11/1966 Koch et al. ..................... 56/14.4
4,925,789 A    5/1990 Edberg
(Continued)

FOREIGN PATENT DOCUMENTS

GB    2220066 A    8/2010
WO    9614431    5/1996
(Continued)

OTHER PUBLICATIONS

Link et al., "Inorganic Nanoparticles for Transfection of Mammalian Cells and Removal of Viruses from Aqueous Solutions", Biotechnology and Bioengineering, vol. 98, No. 5, pp. 1083-1093; 2007.

(Continued)

*Primary Examiner* — Michael Hobbs
(74) *Attorney, Agent, or Firm* — Hoffmann & Baron, LLP (57) ABSTRACT

The present invention relates to a system for detecting microbial contamination of a liquid specimen comprising a device for concentrating micro-organisms from a liquid specimen, having (i) a hyperbaric chamber, (ii) a filter housing comprising a liquid-permeable bed of an adsorbent material and adapted for being fluidly connected to the hyperbaric chamber, and (iii) a manner for pressurizing the hyperbaric chamber. The system also comprises a kit for detection of micro-organisms adsorbed to the adsorbent material, wherein the kit is based on enzymatic detection using chromogenic and/or fluorescent substrate analogues.

26 Claims, 4 Drawing Sheets

(56) References Cited

U.S. PATENT DOCUMENTS

| | | |
|---|---|---|
| 5,429,933 A | 7/1995 | Edberg |
| 5,518,892 A | 5/1996 | Naqui et al. |
| 5,610,029 A | 3/1997 | Ehrenfeld et al. |
| 5,620,865 A | 4/1997 | Chen et al. |
| 5,620,895 A | 4/1997 | Naqui et al. |
| 5,690,825 A | 11/1997 | Parton |
| 5,700,655 A | 12/1997 | Croteau et al. |
| 5,753,456 A | 5/1998 | Naqui et al. |
| 5,756,717 A * | 5/1998 | Paliwal et al. .............. 536/123.1 |
| 5,780,259 A | 7/1998 | Edberg |
| 5,985,594 A | 11/1999 | Croteau et al. |
| 6,287,797 B1 | 9/2001 | Croteau et al. |
| 6,329,166 B1 | 12/2001 | Edberg |
| 6,387,650 B1 | 5/2002 | Townsend et al. |
| 6,472,167 B1 | 10/2002 | Townsend et al. |
| 6,509,168 B2 | 1/2003 | Croteau et al. |
| 6,730,496 B2 | 5/2004 | Edberg |
| 6,783,950 B2 | 8/2004 | Edberg |
| 2003/0039613 A1 * | 2/2003 | Unger et al. ................. 424/9.51 |
| 2004/0185550 A1 * | 9/2004 | Nakajima et al. ........... 435/287.2 |
| 2005/0029196 A1 * | 2/2005 | Rhemrev-Boom ............ 210/656 |
| 2005/0048474 A1 | 3/2005 | Amburgey, Jr. |
| 2007/0037225 A1 | 2/2007 | Metzger et al. |
| 2008/0153125 A1 * | 6/2008 | Buttry et al. .................... 435/30 |

FOREIGN PATENT DOCUMENTS

| | | |
|---|---|---|
| WO | 9947637 | 9/1999 |
| WO | 0013764 | 3/2000 |
| WO | 0159157 A3 | 8/2001 |
| WO | 2005083109 A1 | 9/2005 |

OTHER PUBLICATIONS

Boccaccini et al., "Application of Electophoretic and Electrolytic Deposition Techniques in Ceramics Processing", Current Opinion in Solid State and Materials Science, vol. 6, pp. 251-260; 2002.

Dierstein et al., "Electrochemical Deposition under Oxidizing Conditions (EDOC): A New Synthesis for Nanocrystalline Metal Oxides", Scripta Mater, vol. 44, pp. 2209-2212; 2001.

Ding et al., "Polymer-Monomer Pairs as a Reaction System for the Synthesis of Magnetic Fe3O4-Polymer Hybrid Hollow Nanospheres", Angew. Chem. Int. Ed., vol. 43, pp. 6369-6372; 2004.

M. Manafi, "New Developments in Chromogenic and Fluorogenic Culture Media", International Journal of Food Microbiology, vol. 60, pp. 205-218; 2000.

* cited by examiner

SYSTEM FOR DETECTING MICROBIAL CONTAMINATION

This application is the U.S. National Phase of, and Applicants claim priority from, International Patent Application Number PCT/NL2008/050741 filed 24 Nov. 2008, European Patent Application Number 07121431.6 filed 23 Nov. 2007 and European Patent Application Number 08152030.6 filed 27 Feb. 2008, each of which are incorporated herein by reference.

FIELD OF THE INVENTION

The present invention is in the field of rapid detection of microbial contamination. In particular, the present invention relates to a system for rapid detection of microbial contamination in fluid samples, in particular microbial contamination originating from faeces. A system of the invention comprises a device for concentrating bacteria from a fluid sample as part of a kit for detecting microbial contamination, in particular a kit for detection of micro-organisms adsorbed to an adsorbent material by enzymatic detection using chromogenic and/or fluorescent substrate analogues, and a method for detecting microbial contamination in water specimens using the inventive device.

BACKGROUND OF THE INVENTION

In developing countries many millions of people fall victim to waterborne diseases each year. Yearly about 250 million new cases of waterborne infections are reported world-wide, resulting in 1.8 million fatalities ensuing from diarrhoeal diseases, of which 90% are children under the age of 5. In India alone, yearly 320 thousand children die from diarrhoea. Almost invariably this is due to a lack of reliable and cost-effective water production technology, sanitation and hygiene, resulting in unsafe water or water of poor bacteriological quality. Moreover, there is a lack of systems for assessing the bacteriological quality of water. Use of safe drinking water can reduce diarrhoeal morbidity by between 6 to 25%. If water is unsafe, it can be treated. In fact, chlorination at point of use can decrease diarrhoea by 35 to 39%. Therefore, there is a need for systems for assessing the bacteriological quality of water at the point of use, to determine whether treatment is necessary.

The most common cause of waterborne disease is faecal contamination. Most often, drinking water is contaminated with animal and human excrement. Faecal contamination of drinking water is usually not noticed due to lack of affordable diagnostic methods. In order to detect faecal contamination use can be made of so-called indicator organisms. An indicator organism to detect faecal contamination: i) is universally present in large numbers in the faeces of humans and warm-blooded animals; ii) readily detected by simple methods; iii) exhibits no growth in natural waters; and iv) persists in water and can be removed by water treatment similar to waterborne pathogens. A very suitable faecal indicator organism, and the one designated by the World Health Organization (WHO) for that purpose, is *Escherichia coli*. More precisely, an indication of faecal contamination can be obtained by the determination of the number per 100 ml of water of coliforms (facultatively-anaerobic, rod-shaped, Gram-negative, non-sporulating bacteria that ferment lactose; including for instance species of the genera *Escherichia, Enterobacter, Kebsiella* and *Citrobacter*) and especially the thermotolerant coliform *Escherichia coli*.

With respect to the test system for detecting *Escherichia coli*, the WHO has introduced the acronym ASSURED to describe the ideal properties and criteria of a diagnostic test which stands for: Affordable (for those at risk of infection); Sensitive (few false negatives); Specific (few false positives); User-friendly (simple to perform and requiring minimal training); Rapid (to enable treatment at first visit) and robust (does not require refrigerated storage); Equipment-free; and Deliverable to developing countries. Numerous methods have been used for the detection of coliforms and *E. coli* in water. These detection methods can be based on for instance cultivation, enzyme reaction, and immunological or genetic detection. Currently there are more than 30 alternative assays commercially available to detect coliforms and *E. coli*. Most of these tests do not comply with the ASSURED criteria for speed and sensitivity, or for not being equipment free. In fact, most require a dedicated laboratory in order to meet the most essential test criteria for being sensitive and specific. It should be understood, however, that a rapid field test for faecal contamination that is less sensitive than the laboratory tests may result in a significant reduction of sick people and save lives. Thus, a sensitive laboratory test is not always more useful than a less-sensitive, but rapid and specific field test that does the job, i.e. that tells the user that the water is unsafe to drink.

Thus, there is a need for a simple, cheap, robust and fast test method for on site detection of faecal contamination in water. Such a method will be used more frequently, at more places by more people and can warn people earlier, and as a consequence, save lives.

SUMMARY OF THE INVENTION

The present inventors have now discovered that a diagnostic test system can be developed that is capable of detecting coliforms and *E. coli* and that is simple, cheap, robust and fast and suitable for on site detection of faecal contamination of water specimens. The diagnostic test system combines solid phase adsorption of microbial cells with specific growth and enzymatic detection of adsorbed cells.

In a first aspect, the present invention provides a device for concentrating micro-organisms from a liquid specimen comprising:
  a) a hyperbaric chamber for holding a liquid specimen comprising:
    a liquid inlet through which said liquid specimen can enter said hyperbaric chamber,
    a liquid outlet through which said liquid specimen can leave said hyperbaric chamber and adapted for sealably engaging with the liquid inlet of a filter housing, and
    means for pressurizing said hyperbaric chamber; and
  b) a filter housing comprising:
    a liquid inlet through which said liquid specimen can enter the filter housing and adapted for engaging with the liquid outlet of said hyperbaric chamber,
    a liquid outlet through which said liquid specimen can leave the filter housing, and
    a liquid-permeable bed of an adsorbent material housed in the filter housing between said liquid inlet and liquid outlet of said filter housing and capable of adsorbing micro-organisms by electrostatic interaction,
  whereby when:
  i) said hyperbaric chamber containing a liquid specimen is sealably engaged with said filter housing such that fluid communication between said hyperbaric chamber and said filter housing is allowed by means of a sealed passageway therebetween, and ii) said hyperbaric chamber is pressurized, said liquid specimen is forced into the filter housing from said hyperbaric chamber and passes through said liquid-permeable bed of an adsorbent material before leaving via said liquid outlet.

In a preferred embodiment of a device of the invention the filter housing is essentially cylindrical and translucent at the position of the bed of an adsorbent material, and wherein said housing preferably has an inner volume of between 1 and 10 ml.

In another preferred embodiment of a device of the invention the adsorbent material has a positively charged surface and is selected from the group consisting of insoluble metal hydroxides, metal oxides, metal hydroxides on a support material, metal oxides on a support material, lectins on a support material, carbodiimides on a support material, cationic polymers on a support material, anion exchange resins, and positively charged electrodes.

In the instance that the adsorbent material is based on cationic polymers, such polymers are preferably selected from poly-L-lysine, polyethyleneimine and combinations thereof.

In the instance that the adsorbent material is based on insoluble metal oxides and/or hydroxides, such insoluble metal oxides and/or hydroxides are preferably selected from hydroxyapatite, zirconium hydroxide, titanium hydroxide, manganese hydroxide and hafnium hydroxide, zirconium oxide, titanium oxide, manganese oxide, iron oxide and hafnium oxide. In a preferred embodiment the adsorbent material is hydroxyapatite. In an alternative preferred embodiment the absorbent material is a metal oxide selected from zirconium, hafnium, manganese, titanium or iron oxide.

The liquid from a specimen of which the micro-organisms are concentrated using the device of the instant invention is preferably water, most preferably drinking water.

The liquid inlet and liquid outlet of said hyperbaric chamber are preferably combined into a single port.

In another aspect, the present invention provides a system for detecting micro-organisms in a liquid specimen, comprising:

i) a device for concentrating micro-organisms from a liquid specimen according to the invention as described above;

ii) a kit for the detection of said micro-organisms by detecting enzymatic activity specific for said micro-organism comprising a chromogenic and/or fluorogenic substrate and a liquid growth medium, said substrate preferably being in the form of a supplement for said growth medium; and optionally iii) instructions for assembling, operating and disassembling the device, and/or detecting micro-organisms concentrated in said device by using said detection kit.

In a preferred embodiment of a system of the present invention, the kit is for the detection of coliforms and/or *E. coli* by detecting enzymatic activity of β-D-galactosidase and/or β-D-glucuronidase, respectively.

Suitable chromogenic or fluorogenic substrate for detection of β-D-glucuronidase and/or β-D-galactosidase activity include, but are not limited to 4-methylumbelliferyl-β-D-glucuronide (MUG); ortho-nitrophenyl β-D-glucuronide (ONPG); para-nitrophenyl β-d-glucuronide (PNPG); β-naphthalamide-β-D-glucuronide; 6-bromo-2-naphthyl β-D-glucuronide; 5-bromo-4-chloro-3-indolyl β-D-glucuronide (BCIG or X-glucuronide); α-napthol-β-D-glucuronide; 4-methylumbelliferyl-β-D-galactopyranoside (MU-Gal), ortho-nitrophenyl-β-D-galactopyranoside (ONPGal); para-nitrophenyl-β-D-galactopyranoside (PNPGal); 6-chloro-3-indolyl-β-D-galactopyranoside (Salmon-Gal), 5-bromo-4-chloro-3-indolyl β-D-galactopyranoside (X-Gal); 4-nitrophenyl 1-thio-β-D-galactopyranoside (NPS-Gal), 6-bromo-2-naphthyl-β-d-galactopyranoside; 3,4-dinitrophenyl β-D-galactopyranoside (DNPGal), functional derivatives, and combinations thereof.

Preferably, the liquid growth medium comprises allolactose, isopropyl-β-D-thiogalactopyranoside (IPTG) and/or lactose, in order to induce the enzymes of which the activity is to be detected (i.e. β-D-glucuronidase and/or β-D-galactosidase).

In yet another aspect, the present invention provides a method for detecting micro-organisms in a liquid specimen, said method comprising the steps of:

a) i) providing a hyperbaric chamber for holding a liquid specimen comprising:

a liquid inlet through which a liquid specimen can enter said hyperbaric chamber, a liquid outlet through which said liquid specimen can leave said hyperbaric chamber and adapted for sealably engaging with the liquid inlet of a filter housing, and means for pressurizing said hyperbaric chamber;

ii) providing a filter housing having a liquid inlet and a liquid outlet and housing a liquid-permeable bed of an adsorbent material in between said liquid inlet and said liquid outlet, wherein said adsorbent material is capable of adsorbing micro-organisms by electrostatic interaction;

iii) loading a liquid specimen into said hyperbaric chamber;

iv) sealably engaging said hyperbaric chamber with the liquid inlet of said filter housing such that fluid communication between said hyperbaric chamber and said filter housing is allowed by means of a sealed passageway therebetween;

b) pressurizing said hyperbaric chamber loaded with said liquid specimen, thereby forcing said liquid specimen from said hyperbaric chamber into said filter housing whereby said liquid specimen passes through said liquid-permeable bed of an adsorbent material before leaving said filter housing via said liquid outlet and adsorbing onto the liquid-permeable bed of an adsorbent material said micro-organisms present in said liquid specimen;

c) continue pressurizing said hyperbaric chamber until an effective amount of said liquid specimen has passed through said liquid-permeable bed of an adsorbent material;

d) incubating for an effective period of time said liquid-permeable bed of an adsorbent material with a liquid growth medium supplemented with a chromogenic and/or fluorogenic substrate in order to detect enzymatic activity of micro-organisms; and e) monitoring the development of a chromogenic or fluorescent color to establish the presence or absence of micro-organisms adsorbed to adsorbent material, wherein the presence of micro-organisms adsorbed to said adsorbent material indicates the presence of micro-organisms in said liquid specimen.

In a preferred embodiment of a method of the invention the filter housing is essentially cylindrical and translucent at the position of the bed of an adsorbent material, and wherein said housing preferably has an inner volume of between 1 and 10 ml.

In another preferred embodiment of a method of the invention the adsorbent material has a positively charged surface and is selected from the group consisting of insoluble metal hydroxides, metal oxides, metal hydroxides on a support material, metal oxides on a support material, lectins on a support material, carbodiimides on a support material, cationic polymers on a support material, anion exchange resins, and positively charged electrodes.

In the instance that the adsorbent material is based on cationic polymers, such polymers are preferably selected from poly-L-lysine, polyethyleneimine and combinations thereof.

In the instance that the adsorbent material is based on insoluble metal hydroxides, such insoluble metal hydroxides are preferably selected from hydroxyapatite, zirconium hydroxide, titanium hydroxide and hafnium hydroxide. In a most preferred embodiment the adsorbent material is hydroxyapatite.

The liquid in a specimen of which the micro-organisms are detected using the method of the instant invention is preferably water, most preferably drinking water.

The means for pressurizing said hyperbaric chamber may be a syringe-type piston, or a deformable chamber wall allowing compression of the chamber volume by deforming its walls.

In further preferred embodiments of the invention, the liquid growth medium and the chromogenic and/or fluorogenic substrate are for the detection of coliforms and/or $E.$ $coli$ by detecting enzymatic activity of $\beta$-D-galactosidase and/or $\beta$-D-glucuronidase, respectively. For that purpose, a method of the invention may very suitably be performed by selecting a chromogenic or fluorogenic substrate from the group consisting of 4-methylumbelliferyl-$\beta$-D-glucuronide (MUG); ortho-nitrophenyl $\beta$-D-glucuronide (ONPG); para-nitrophenyl $\beta$-d-glucuronide (PNPG); $\beta$-naphthalamide-$\beta$-D-glucuronide; 6-bromo-2-naphthyl $\beta$-D-glucuronide; 5-bromo-4-chloro-3-indolyl $\beta$-D-glucuronide (BCIG or X-glucuronide); $\alpha$-napthol-$\beta$-D-glucuronide; 4-methylumbelliferyl-$\beta$-D-galactopyranoside (MUGal), ortho-nitrophenyl-$\beta$-D-galactopyranoside (ONPGal); para-nitrophenyl-$\beta$-D-galactopyranoside (PNPGal); 6-chloro-3-indolyl-$\beta$-D-galactopyranoside (Salmon-Gal), 5-bromo-4-chloro-3-indolyl $\beta$-D-galactopyranoside (X-Gal); 4-nitrophenyl 1-thio-$\beta$-D-galactopyranoside (NPSGal), 6-bromo-2-naphthyl-$\beta$-d-galactopyranoside; 3,4-dinitrophenyl $\beta$-D-galactopyranoside (DNPGal), functional derivatives, and combinations thereof.

In a preferred embodiment of a method of the invention, the liquid growth medium comprises allolactose, isopropyl-$\beta$-D-thiogalactopyranoside (IPTG) and/or lactose.

In yet another preferred embodiment, the presence of micro-organisms adsorbed to the adsorbent material is indicative of a potential contamination of said liquid specimen with faecal bacteria.

DETAILED DESCRIPTION OF THE INVENTION

Definitions

The term "micro-organism", as used herein, refers to a diverse group of minute, simple life forms that include archeae, bacteria, yeast, algae, fungi, protozoa, and viruses.

The term "insoluble metal hydroxides" includes reference to hydroxyapatite.

The term "hydroxyapatite" and the abbreviation "HA", as used herein, refer to a hydroxylated calcium phosphate, in particular to the substance known as hydroxyapatite per se $(Ca_{10}(PO_4)_6(OH)_2$ or $Ca_5(PO_4)_3OH$, synonym: (penta)calcium triphosphate having a (stoichiometric) Ca/P ratio of 1.67), but also to:

calcium-deficient hydroxyapatite $Ca_{10-x}(HPO_4)_x(PO_4)_{6-x}(OH)_{2-x}$ ($0 \leq x \leq 1$) with Ca/P ratio varying from 1.4 to 1.67;

simulated, synthetic or precipitated hydroxyapatite (PHA) having a Ca/P molar ratio of 1.4-1.8 hydroxyapatite containing traces of fluor, chlorine and/or carbonate mixtures of two or more of the above composites comprising one of the above The terms "fluidly connected" and "fluid communication", as used herein, are equivalent and refer to the presence of a passageway providing a sealed communication that permits passage of liquids and/or gases between items thus connected.

Figure 1:
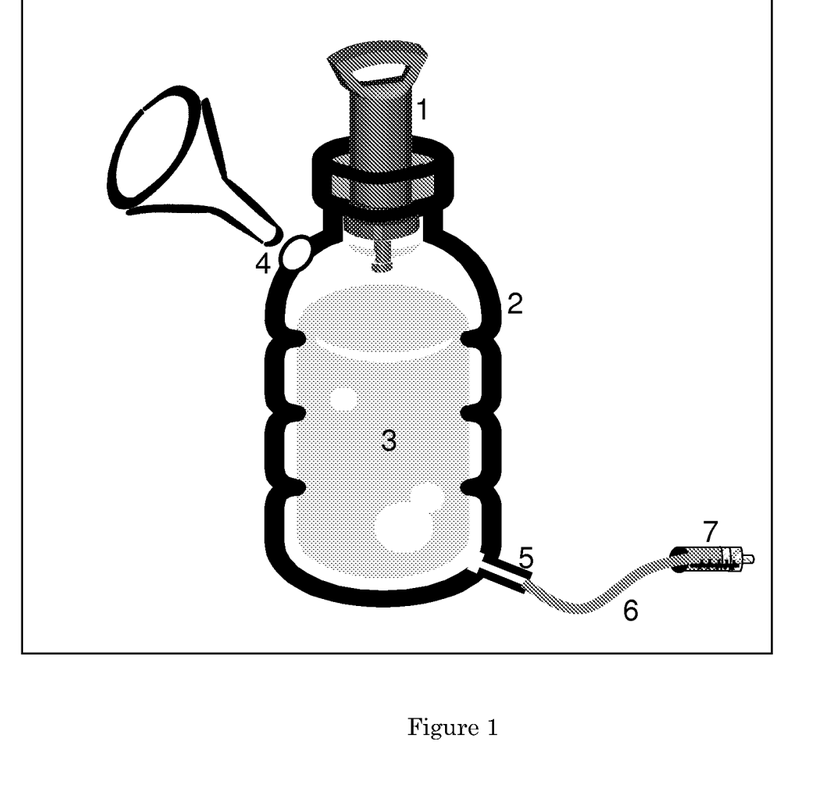
FIG. 1 illustrates a device according to the present invention indicating the various elements: pressure pump (1), hyperbaric chamber (2), water sample (3), liquid inlet (4) (illustrated with a funnel for filling), liquid outlet (5), connective tubing (6), filter housing (7). The skilled person will understand that the liquid inlet may also be formed by an opening in the top of the vessel where the pressure pump is mounted and which first becomes accessible after removal of the pressure pump.
Figure 2:
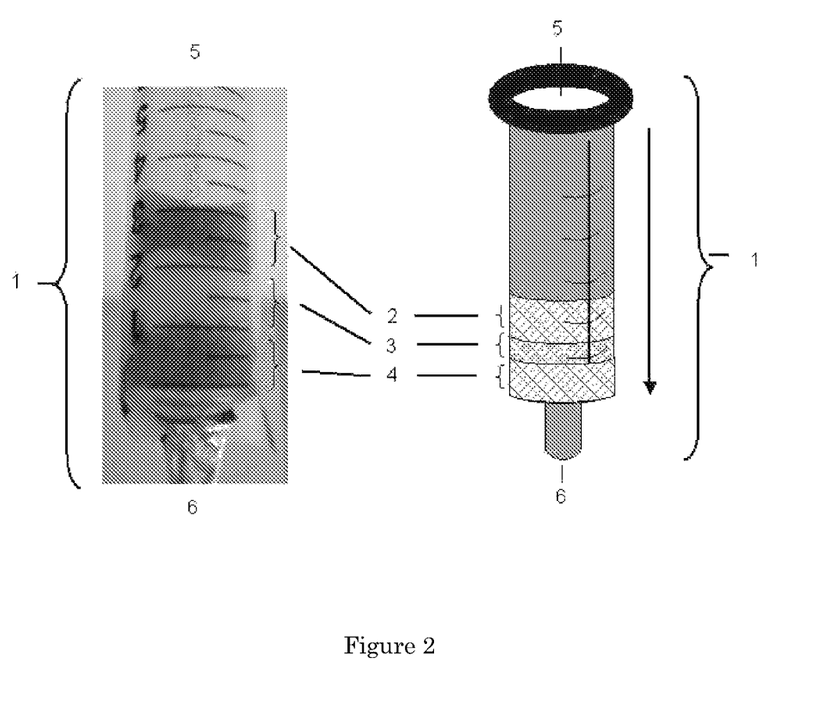
FIG. 2 shows a photograph (left) and a schematic drawing (right) of the filter housing of the present invention, indicating the various elements in more detail. Filter housing (1) (in this photograph a disposable syringe), pre-filter (coarse) (2), bed of adsorbent material (3), post-filter (fine) (4), liquid inlet (5), liquid outlet (6). The direction of the flow of the liquid specimen is indicated by an arrow.
Figure 3:
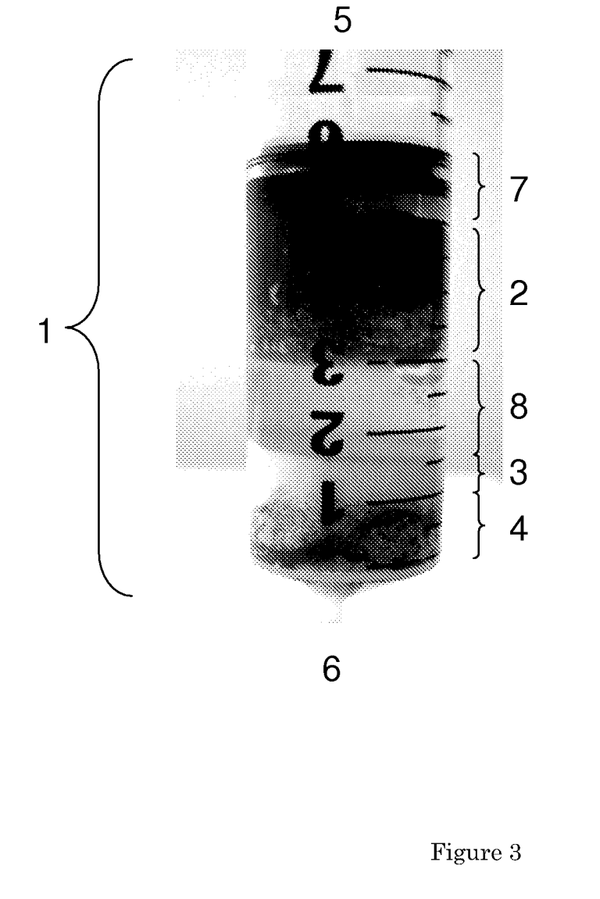
FIG. 3 shows a photograph of the filter housing (1) (in this photograph a disposable syringe), pre-filter (coarse) (2), bed of adsorbent material (3), post-filter (fine) (4), liquid inlet (5), liquid outlet (6). The filter was used to process 10 L of liquid specimen with $E.$ $coli$. A syringe plunger (7) was used to draw chromogenic culture liquid (in this case Colilert®) into the filter housing through the liquid outlet in the direction indicated by an arrow. After incubation for several hours at 37° C. the chromogenic liquid has changed from a clear solution into a yellow coloured solution due to metabolic conversion by de micro-organism.
Figure 4:
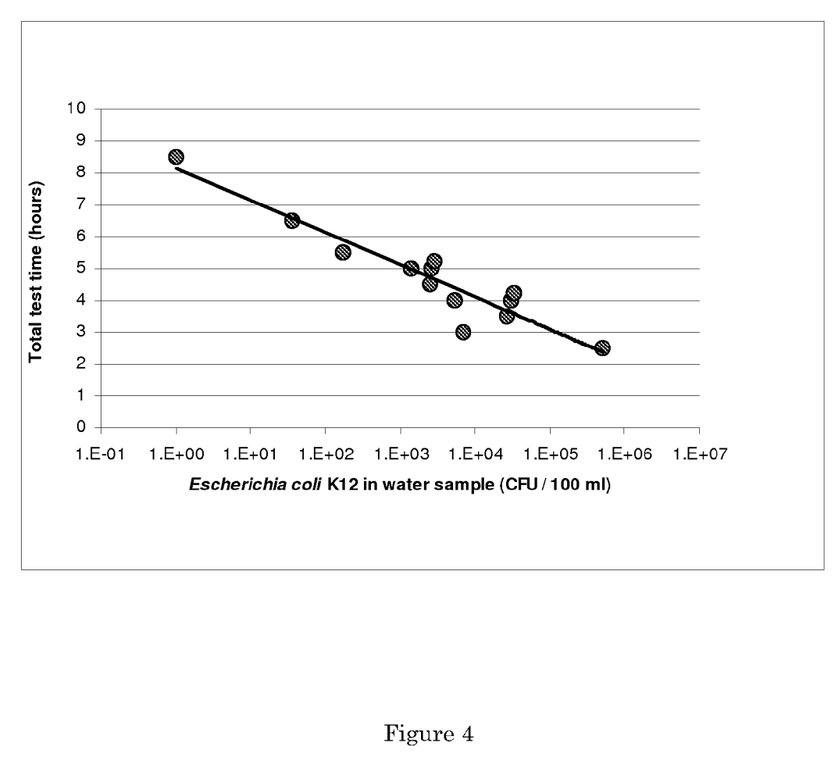
FIG. 4 shows the total time from the start of sampling until the observation of a positive test result (in this case a yellow colour), depending on the concentration of viable $Escherichia$ $coli$ strain K12 bacteria in a liquid specimen (test sample). This total test time includes the filtration of the 10 L liquid specimen and incubation with a chromogenic solution (in this case Colilert®) at 37° C. For this test the $E.$ $coli$ bacteria were pre-grown in Tryptic Soy Broth medium (Oxoid) and diluted in a physiological salt solution (0.9% NaCl) to the appropriate test concentrations.

The present invention relates to a system for detecting microbial contamination of a liquid specimen comprising a device for concentrating micro-organisms from a liquid specimen essentially as displayed in FIG. 1 (the numbers indicate the reference numbers in FIG. 1), consisting essentially of separate parts that may be interconnected and disconnected, or that may be assembled and combined by integration into a single part. These separate parts include means for creating hyperbaric conditions in a hyperbaric chamber (e.g. an air pump, a slope of water, hydropower caused by hydraulic head allowing water to be pressurized), a hyperbaric chamber and a filter housing comprising the liquid-permeable bed of an adsorbent material.

WO2005/083109 describes a method of sample preparation wherein contaminants suspected of being present in the sample are retained on one side of a filter. The filter in WO2005/083109 can take the form of a column for affinity chromatography. Affinity chromatography is a chromatographic method of separating biochemical mixtures, based on a highly specific biologic interaction such as that between antigen and antibody, or receptor and ligand.

The present invention is based on the use of electrostatic interaction for the binding of micro-organisms. Such binding by electrostatic interaction may for instance be obtained by use of ion-exchange resins. Ion-exchange chromatography is a process that separates ions; the basis of the separation is the varying attraction of different ions in a solution to oppositely charged sites on a finely divided, insoluble substance (the ion exchanger, usually a synthetic resin). In a cation-exchange resin all the sites are negatively charged, so that only positive ions can be separated; an anion-exchange resin has positively charged sites, so that only negatively charged ions can be separated.

As clearly indicated in Example 1 herein below, the use of positively charged particles, such as metal oxides or hydroxyapatite results in very effective binding of *E. coli* cells. The use of a cation-exchange resin, wherein all the sites are negatively charged, appears less effective for binding of *E. coli* cells. However, this does not mean that cationic exchange resins are unsuitable for use in aspects of the present invention. In fact, cells other than *E. coli*, and similar cells grown or treated (adsorbed) under different conditions, may successfully be adsorbed to such resins.

The device of the present invention may in principle take any shape, form or configuration suitable. Alternatively, the means for creating hyperbaric conditions in a hyperbaric chamber and the hyperbaric chamber itself may be combined, such as by providing the hyperbaric chamber with compressible walls or providing said hyperbaric chamber with a piston assembly in slidable, sealable contact with the interior surface of a tubular hyperbaric chamber thereby expanding or reducing the inner volume of said hyperbaric chamber. The hyperbaric chamber need not be separately provided, and may for instance constitute a part of the pressure means, such as when these pressure means are provided in the form of a water pump or a slope of water (ie. water under pressure). It should be understood that in such a configuration the hyperbaric chamber is comprised in the pressure means.

The liquid specimen may be any type of liquid, but is preferably water.

The system of the invention can be operated using very simple methods. The parts of the device must be functionally interconnected. This can be achieved by connecting the air outlet of the air pump and the liquid inlet of the filter housing via a suitable conduit, such as a flexible tubing, to separate ports of a hyperbaric chamber. The device of the present invention may thus be easily assembled and disassembled.

For operation, the hyperbaric chamber is loaded with a liquid specimen, and hyperbaric conditions are created in the hyperbaric chamber by activating the pressurizing means. As a result, the liquid specimen will be forced into the filter housing and will pass the absorbent material.

In an alternative embodiment, a liquid inlet of an otherwise sealed tubular hyperbaric chamber fitted with a piston assembly in slidable, sealable contact with the interior surface of said chamber is brought into contact with a liquid specimen and the piston is actuated to enlarge the interior volume of said chamber thereby creating hypobaric conditions in said chamber as a result of which liquid is drawn into said hyperbaric chamber. Subsequently, or in advance, the liquid inlet of a filter housing is sealably engaged with the liquid outlet of said hyperbaric chamber and the piston is actuated to reduce the interior volume of said chamber thereby creating hyperbaric conditions in said chamber as a result of which liquid is forced out of said hyperbaric chamber via said outlet and into said filter housing.

The device of the present invention thus comprises a hyperbaric chamber. The term refers to a space in which a relative pressure can be established. The chamber is an essentially closed element of any shape (vessel, flask, tubing or funnel) having at lease one port serving as an inlet and outlet for the liquid specimen. Very suitably, the chamber is formed by the interior of a housing having an essentially cylindrical side wall (hyperbaric chamber wall) and having an open top end in which a piston can be inserted, and bottom end wherein a liquid inlet and outlet is provided. The liquid inlet and air outlet may in principle be positioned in the wall, top or bottom end of the chamber, but are preferably provided in the bottom end of the chamber opposite the piston.

The hyperbaric chamber is provided with a liquid inlet through which a liquid specimen can enter the hyperbaric chamber and adapted for engaging with said liquid specimen. Such an adaptation may include a tip or a port connected to a tubing that can be submerged below the liquid surface. It should be noted that due to this adaptation, systems and methods of the invention as described herein below in more detail, do not require the provision of a sample. In fact, the device can be contacted directly with the water body of which the potential faecal contamination is to be determined. This increases the reliability of the systems and methods.

The hyperbaric chamber is further provided with a liquid outlet through which said liquid specimen can leave the hyperbaric chamber. The liquid outlet is adapted for sealably engaging with a filter housing. Such an adaptation may comprise a port for the connection of tubing.

The liquid inlet and liquid outlet may be combined into a single port.

The purpose of the hyperbaric chamber is to provide a relative pressure extending via the liquid inlet of the filter housing, via the liquid-permeable filter bed to the liquid outlet of the filter housing to force the liquid specimen through the absorbent material. The purpose of the hyperbaric chamber is further to provide a relative pressure of essentially constant level in order to provide for a constant flow of liquid through the liquid-permeable bed of adsorbent material.

The hyperbaric chamber is preferably provided in a sterile (aseptic) packaging, which allows transport and storage without pre-mature contamination of the hyperbaric chamber. For assembly of the device of the present invention, the sterile hyperbaric chamber is preferably removed aseptically from the sterile packaging and connected aseptically to the remainder of the device.

The hyperbaric chamber may be of any suitable rigid material such as glass, metal, polystyrene, acrylic polymer, polyamide, polyethylene, polypropylene, acrylate butadiene styrene (ABS), polyvinylchloride (PVC), nylon, ethylene-vinyl acetate (EVA), polyethylene terephthalate (PET) and combinations thereof. The material may for instance be all clear, white, black or transparent or light-blocking and may in principle be of any colour. The hyperbaric chamber is preferably essentially cylindrical and translucent. The hyperbaric chamber needs not be very large, in fact a conventional syringe is very suitable for use as the hyperbaric chamber. Such a syringe can have an inner volume of between 1 and 100 ml. Generally, an inner volume of between 10 and 25 ml may be sufficient. However, large volumes of 1-100 L are also possible, provided they can be sufficiently pressurized and sterilized.

The device of the present invention further comprises a filter housing. The filter housing is preferably provided in a sterile (aseptic) packaging, which allows transport and storage without pre-mature contamination of the filter housing. For assembly of the device of the present invention, the sterile filter housing is preferably removed aseptically from the sterile packaging and connected aseptically to the remainder of the device.

The filter housing may be of any suitable rigid material such as glass, metal, polystyrene, acrylic polymer, polyamide, polyethylene, polypropylene, acrylate butadiene styrene (ABS), polyvinylchloride (PVC), nylon, ethylene-vinyl acetate (EVA), polyethylene terephthalate (PET) and combinations thereof. The material may for be all clear, white, black or transparent or light-blocking and may in principle be of any colour. The filter housing is preferably essentially cylindrical and translucent at an area between 1 to 5 cm surrounding the position of the bed of adsorbent material, enabling (visual) monitoring of the chromogenic reaction. The filter housing needs not be very large, in fact a conventional syringe is very suitable for use as the filter housing. Such a syringe can have an inner volume of between 1 and 100 ml. Generally, an inner volume of between 1 and 10 ml may be sufficient to house an amount of adsorbent material capable of adsorbing the microorganisms from as much of 20 litres of water.

The filter housing is provided with a liquid inlet through which said liquid specimen can enter the filter housing and adapted for engaging with said liquid specimen. Such an adaptation may include a tip or a port connected to a tubing that can be submerged below the liquid surface. It should be noted that due to this adaptation, systems and methods of the invention as described herein below in more detail, do not require the provision of a sample. In fact, the device can be contacted directly with the water body of which the potential faecal contamination is to be determined. This increases the reliability of the systems and methods.

The filter housing is further provided with a liquid outlet through which said liquid specimen can leave the filter housing. The liquid outlet is adapted for sealably engaging with a hyperbaric chamber. Such an adaptation may comprise a port for the connection of tubing.

The filter housing is further provided with a liquid-permeable bed of an adsorbent material. In order to be liquid-permeable, the adsorbent material may be porous or may take the form of a granulate wherein the liquid can flow through the space between the granules. Pores will suitably have a size of between 5 µm and 1 mm. Also the granules may have a size of between 1 µm and 5 mm, more preferably between 5 µm and 1 mm. The adsorbent material is preferably housed in the filter housing in the form of a bed through which the liquid must pass. The term bed merely refers to the fact that the liquid cannot flow next to the absorbent material, but that it will flow through the intra- and/or extragranular pores of said bed and comes into contact with the surface of the absorbent material, while flowing from the inlet to the outlet. Practically, the bed may be housed in the cylindrical housing in the form of a disk having a thickness of 0.1-10 cm, and a diameter equal to the inner diameter of the filter housing.

The adsorbent material is capable of adsorbing microorganisms. Any material, of which it is known that microorganisms can adsorb to it, can be used. Preferably, the microorganisms are adsorbed by means of electrostatic interaction, i.e., by charge difference. To that effect, the adsorbent material may suitably be based on insoluble metal hydroxides such as hydroxyapatite, zirconium hydroxide, titanium hydroxide and hafnium hydroxide; metal oxides, metal hydroxides on a support material, metal oxides on a support material; lectins on a support material; carbodiimides covalently conjugated to a support material, preferably particulate material with a size of between 5 µm and 1 mm; cationic (positively charged) polymers on a support material such as poly-L-lysine, polyethyleneimine and combinations thereof; anion exchange resins; and positively charged electrodes. Other positively charged adsorbent materials which may be used are materials comprising metal oxides wherein the metal is selected from aluminium, calcium, cerium, hafnium titanium, iron, manganese and zirconium. These materials may be produced cost-effectively in large amounts as inorganic nanoparticles using flame-spray synthesis technology and are known to effectively adsorb and remove DNA and viruses from water (Link et al., 2007, Inorganic nanoparticles for transfection of mammalian cells and removal of viruses from aqueous solutions. Biotechnology and Bioengineering 98(5)1083-1093). The highly adsorbent nanoparticles may have a specific surface area between 50 and 250 $m^2 g^{-1}$ and a particle size between 5 and 50 nm and filtration and micro-organism removal may be most effective when they are deposited on a support material (Boccaccini and Zhitomirski, 2002, Application of electrophoretic and electrolytic deposition techniques in ceramics processing. Current Opinion in Solid State and Materials Science 6:251-260; Dierstein et al., 2001, Electrochemical deposition under oxidizing conditions (EDOC): a new synthesis for nanocrystalline metal oxides. Scripta mater. 44:2209-2212; Ding et al., 2004, Polymer-Monomer pairs as a reaction system for the synthesis of magnetic $Fe_3O_4$-Polymer hybrid hollow nanospheres. Angew. Chem. Int. Ed. 43:6369-6372). Negatively charged adsorbent materials, such as cation exchange resins, can also be used in certain embodiments.

In preferred embodiments the adsorbent material is hydroxyapatite, metal oxide powder, and/or metal hydroxide powder. Even more preferred are hydroxyapatite powder and/or metal oxide powder. Suitable forms of hydroxyapatite, metal oxide powder, and/or metal hydroxide powder are crystalline or ceramic granular or particulate hydroxyapatite, metal oxide powder, and/or metal hydroxide powder, typically having a (spherical) particle size of between 5 µm and 1 mm. The hydroxyapatite, metal oxide powder, and/or metal hydroxide powder may be in a macroporous form, wherein a pore size of between 5 µm and 1 mm is suitable. Particle sizes and pore sizes of the adsorbent (and/or support) material may be adjusted to control the flow of liquid through the bed of adsorbent material. Most preferred materials for use as adsorbent material in aspects of this invention exhibit attachment percentages exceeding 36%, more preferably 40%, still more preferably 80%, when using the test conditions exemplified in Example 1, below. These conditions include that at least the indicated percentage of cells in a cell suspension of approximately $1.10^6$ cells/ml in 0.9 wt. % NaCl becomes attached within a period of 15 minutes under agitation at room temperature to the absorbent material provided as a powder with particles between 1 µm and 1 mm at approximately 3 wt. % in said suspension.

As a support material use can be made of hydroxyapatite, metal oxide, and/or metal hydroxide spheres, or any other mineral particles of the appropriate size. Suitable particles include particles prepared from inorganic materials, such as silicates, glass, metal, ceramics, and clay minerals; and particles of organic materials, such as paper, wood, latex or synthetic polymers (e.g. plastics). The particles should have an approximate size between 5 μm and 1 mm. The particles may be solid or porous.

Alternatively, as a support material, an open-cell foam or wadding (a soft mass or sheet of fibres) of synthetic material, with pore sizes between 5 μm and 1 mm, may be used, such as stone wadding, polyurethane, neoprene, polyolefin or paper.

In order to prevent clogging of the liquid-permeable bed of adsorbent material and to keep the bed in place, a pre-filter may be placed in front of the adsorbent material (that is in the direction of the liquid inlet). Such a pre-filter may for instance be made of porous polyurethane (open cell) foam, porous neoprene, porous polyolefin or stone wadding.

In order to prevent inadvertent removal of the adsorbent material from the bed as a result of the liquid flow, especially when the adsorbent material is provided in granular form, a post-filter may be placed at the back of the adsorbent material (that is in the direction of the liquid outlet). Such a post-filter may for instance be made of porous polyurethane (open cell) foam, porous neoprene, porous polyolefin or stone wadding.

Suitable pre- and post-filters have a surface size so as to essentially cover the bed of adsorbent material on either side. The thickness of the pre- and post-filters may be 0.1 to 10 cm or more.

The device of the present invention further comprises means for creating hyperbaric conditions in the hyperbaric chamber. The purpose of the means for creating hyperbaric conditions in the hyperbaric chamber is to force the liquid specimen out of the hyperbaric chamber. Thus, the hyperbaric chamber is also a reservoir for the liquid specimen. The means for creating hyperbaric conditions in the hyperbaric chamber, are not specifically limiting. Generally an air pump engaged with the hyperbaric chamber such that air may enter said chamber and pressurize it is suitable. Generally, when using air to drive out the liquid specimen, requires the liquid specimen to be positioned in contact with the liquid outlet in order to avoid the escape of air from the hyperbaric chamber. Alternatively, the means may take the form of a piston that is in sealing and sliding contact with the walls of the hyperbaric chamber and that can be engaged or actuated to pressurize the hyperbaric chamber such that a relative pressure differential is generated between the interior of the hyperbaric chamber and the exterior which extends via the liquid outlet.

In another alternative embodiment, the means for pressurizing said hyperbaric chamber may take the form of a deformable chamber wall allowing compression of the chamber and reduction of the chamber's inner volume. When the hyperbaric walls are squeezed or external pressure is applied to them to pressurize the hyperbaric chamber a relative pressure differential will be generated between the interior of the hyperbaric chamber and its exterior which extends via the liquid outlet.

When sealably engaged with the filter housing, this pressure differential will extend across the filter housing (where the pressure at the location of the liquid outlet will be essentially atmospheric, and where the pressure at the location of the liquid inlet is essentially above atmospheric). A small pressure differential will usually be sufficient to obtain the required result of forcing the liquid specimen through the liquid-permeable bed of an adsorbent material. A pressure differential across the filter housing may be in the order of 3800 to 76 torr (wherein 760 torr equals 760 mm Hg @ 0° C. or 1 atm abs or ca. 1013 mbarA or 101.325 kPa), preferably pressures between 760 and 228 torr work well.

The term "system" as used herein refers to an arrangement of materials optionally in combination with a particular method of use of that arrangement to achieve the objective. A system for detecting micro-organisms in a liquid specimen according to the present invention comprises the device as described above and a kit for the detection of said micro-organisms. The term "kit", as used herein, refers to a multitude of components or any combination of elements or interrelated parts, provided together in any form, preferably by providing them in a common package or alternatively by providing at least one component with usage instructions, preferably in printed form, referring to at least one other component, necessary for detecting enzymatic activity specific for the micro-organism that is to be detected.

The kit will generally comprise a chromogenic and/or fluorogenic substrate, suitably incorporated into a suitable growth medium, for supporting the proliferation of the microorganism, and optionally instructions for assembling, operating and disassembling the device, and/or detecting microorganisms concentrated in said device by using the detection kit. In order to induce the expression of the enzyme that is to be detected, specific inducers may be added to the growth medium (herein referred to as enzyme inducing agents). In the case of coliforms and *E. coli* wherein the detection of the lactose-converting enzymes is tested, the liquid growth medium may suitably comprise such inducers as allolactose, isopropyl-β-D-thiogalactopyranoside (IPTG) and/or lactose.

Kits for the detection of micro-organisms based on a chromogenic and/or fluorogenic substrate are well known in the art, and use can be made of any of several commercial kits available from various suppliers. A very suitable kit for the detection of thermotolerant coliforms and *E. coli* is the Colilert® Testkit (IDEXX Laboratories, Inc., Westbrook, Me., USA). More information about Colilert® Tests can be found in U.S. Pat. Nos. 4,925,789; 5,429,933; 5,518,892; 5,610,029; 5,620,865; 5,620,895; 5,690,825; 5,700,655; 5,753,456; 5,780,259; 5,985,594; 6,287,797; 6,329,166; 6,387,650; 6,472,167; 6,509,168; 6,730.496; and 6,783.950. Other chromogenic kits that work well are Colilert, Colisure (IDEXX, USA); ColiComplete (Biocontrol, USA); Fluorocult LMX, Readycult coliforms (Merck, Germany); E. colite (Charm Sci., USA) and B2P Coliquik (B2P Limited, New Zealand), m-Coliblue (Hach, USA) (Manfani, 2000, New developments in chromogenic and fluorogenic culture media. International Journal of Food Microbiology 60:205-218).

The instructions for use of the device and the detection kit may comprise the general outline of the method of the present invention for detecting micro-organisms in a liquid specimen as described herein.

A method of the invention for detecting micro-organisms in a liquid specimen preferably makes use of a device of the invention. The device is assembled by fluidly connecting the separate elements of the device. The method commences with engaging the liquid inlet of the filter housing with the liquid specimen and pumping air into said hyperbaric chamber via an air outlet using a air pump in any order.

Correct assembly of the device and generation of the hyperbaric conditions in the hyperbaric chamber will result in a relative pressure extending to the liquid outlet of the filter housing, which will then force the liquid into the filter housing. When the liquid has filled the filter housing, the hyperbaric conditions in the hyperbaric chamber are maintained and a pressure differential across the filter housing will result that extends to the atmospheric exterior of the filter housing's liquid outlet thereby forcing the liquid to pass through the bed of adsorbent material before it will leave the filter housing via said liquid outlet. The pressure differential across the filter housing resulting from the pressurization of the hyperbaric chamber, and the contact between the liquid specimen and the liquid inlet of the filter housing is maintained until sufficient liquid has passed through the bed of adsorbent material.

As used herein, the skilled person will understand that the effective amount of the liquid specimen that needs to be filtered depends largely on the load in the liquid specimen of the micro-organism that is to be detected. Small loads (low contamination levels) will require concentration of the micro-organisms from large volumes of liquid in order to obtain a number of adsorbed micro-organisms that can be detected using minimal incubation periods for growth of the micro-organism. Alternatively, when long incubation periods for growth of the micro-organism are not problematic, a small number of adsorbed micro-organisms can still result in a positive detection result, even when small volumes of liquid have been analyzed.

In a method of the invention it is preferred that the volume of liquid that is analysed (passed through the bed of adsorbent material) is large (1-100 litres) in order to minimize the time required for additional cultivation of the adsorbed micro-organisms.

The relative pressure generated in the hyperbaric chamber is preferably such that the flow through the bed of adsorbent material is about 50 to 150 m/h. Generally a flow of 100 m/h (calculated as the amount of liquid pumped through the filter bed (the granular bed of adsorbent material) per unit of time (in L/h) times the surface area of the filter bed through which the liquid passes (e.g. a filter bed positioned in a cylindrical housing having a radius of 0.69 cm having a surface area of the $\pi r^2 = 1,5$ cm$^2$)) is slow enough to achieve an adsorption efficiency of micro-organisms on the adsorbent that exceeds 80%, while rapid enough to allow the filtration of 1-100 litres, preferably about 10-50, most preferably about 5-15 litres of liquid, typically in less than 30 minutes.

Once the desired amount of liquid has been passed through the bed of adsorbent material, the bed of an adsorbent material with the micro-organisms adsorbed thereto is incubated with a liquid growth medium supplemented with a chromogenic and/or fluorogenic substrate. Alternatively, the chromogenic and/or fluorogenic substrate may be covalently bound to the filter bed material.

For this step suitable use is made of the liquid growth medium supplemented with a chromogenic and/or fluorogenic substrate as provided by a commercial kit as described above. The incubation commences by contacting the adsorbent material with the supplemented growth medium. This may for instance be achieved by disconnecting the filter housing from the hyperbaric chamber, draining the filter housing of residual liquid from said liquid specimen and adding supplemented growth medium to the bed of adsorbent material the, for instance by using a needle and syringe. Alternatively, a syringe filled with the supplemented growth medium can be assembled to a port of the filter housing to fill the filter housing with said medium and to soak the adsorbent material with supplemented growth medium.

The incubation, which is preferably performed at about 30-45, most preferably around 37° C. to determine total coliform and/or E. coli bacteria, is performed for an effective period of time. A temperature of 44-45° C. is preferred to determine thermotolerant coliforms and/or E. coli. The skilled person will readily understand that the duration of said effective period of time depends largely on the load on the adsorbent material of the micro-organism that is to be detected. Suitable periods may be determined by routine experimentation. Generally, a period of about 1-8 hours, typically 2-6, most typically 3-4 hours is an effective period in order to detect enzymatic activity of micro-organisms.

An important advantage of the device and method of the present invention is that after concentration of the micro-organisms in the filter housing and addition of the liquid growth medium, the entire filter housing may for instance be placed under the armpit of a human to provide for the required incubation temperature of around 37° C. (i.e. 36-38° C.).

During the incubation period, wherein the micro-organisms are allowed to grow and metabolise the chromogenic and/or fluorogenic substrate, the process of colour or fluorescence development can be monitored, either visually using suitable illumination, or by using suitable fluorescence detection equipment. The development of a colour in the filter housing at and/or around the area of the bed of adsorbent material indicates the presence of micro-organisms adsorbed to adsorbent material, derived from said liquid specimen.

A method of the invention may be performed multiple times on the same liquid specimen. Reliable testing requires representative sampling. The recommended minimal number of microbiological analyses depends on the population supplied with water from a specific drinking water source. WHO guidelines require roughly 1 analysis per month per 5,000 individuals using the water.

The invention is illustrated in more detail in the Drawings and by the following non-limiting examples.

EXAMPLES

Example 1

Adsorbent Materials

An amount of 0.5 ml of an overnight liquid culture of E. coli cells (strain K12) was suspended in 4.5 ml of saline (0.9 wt. % NaCl) in a test tube containing an amount of 0.5 ml of a suspension of an adsorbent material to be tested for cell-adsorbing properties. The following suspensions were used. Suspensions of 30 wt % (2 grams in 5 ml saline (0.9% NaCl)) were prepared from the oxides, the sand and the perlite. The suspensions from the Ion Exchange Media Sampler Pack were used as provided by the manufacturer or, in the case of powder, suspended at 30 wt. % in saline. An amount of 0.5 ml of the said suspensions was added to 5 ml of test culture (0.5 ml culture+4.5 ml saline).

Titanium oxide (as Titanium(IV) oxide, technical, ≥99%; Sigma Aldrich Cat. No. 14021_Riedel);

Zirconium oxide (as Zirconium(IV) oxide, powder, 5 µm, 99% trace metals basis; Sigma Aldrich Cat. No. 230693_Aldrich);

Hafnium oxide (as Hafnium(IV) oxide, powder, 98%, Sigma Aldrich Cat. No. 202118_Aldrich);

Iron oxide (as Iron(III) oxide, red, purified, ≥95%; Sigma Aldrich Cat. No. 12342)

Manganese oxide (as Manganese(IV) oxide, ≥90%, powder Sigma Aldrich Cat. No. 13242)

Hydroxyapatite 80 µm; (as CHT® Ceramic Hydroxyapatite Type I Cat. No. 157-0080 BioRad Laboratories, Hercules, Calif., USA)

Perlite (as Agra-perlite, 100 liter, Pull Rhenen B. V., Rhenen, The Netherlands

Media Sampler Pack (Cat no 158-0100 BioRad Laboratories, Hercules, Calif., USA; consisting of: Macro-Prep High Q, DEAE, High S, and CM, 25 ml each; CHT ceramic hydroxyapatite Types I and II, 10 g each; UNOsphere Q and S, 25 ml each; and Macro-Prep methyl HIC and t-butyl HIC, 25 ml each);

Dynabeads® Streptavidin 1 (=M-280) and 2 (=MyOne™ Streptavidin C1) (Invitrogen Corporation, Carlsbad, Calif., USA)

The mixture of cells and test adsorbent material in saline was agitated for 15 minutes. After 15 min. the test adsorbent material (with attached *E. coli* cells) was pelleted by centrifugation (20' @ 500 rpm) and the supernatant containing the freely suspended, unattached cells, was decanted and the pellet was retained for use in Example 2 (below). The cells in the supernatant were counted as colony forming units (CFU) using serial dilutions and a standard plate counting technique. The attachment of the cells to the test adsorbent material was expressed as percentage attached using the formula (X−Y)*100%, wherein X is the number of CFUs in a control aliquot of the culture not including the test adsorbent material, and Y is the number of CFUs in the supernatant of a test culture including the test adsorbent material. The % attachment is indicated in Table 1 below.

The most effective materials in this test were metal oxide particles. These particles are—similar to hydroxyapatite—positively charged, indicating that the adsorption is by electrostatic interaction between the bacterial cells and the adsorbent material. Materials that do not or hardly bind the *E. coli* cells include the uncharged (sand) or negatively charged (perlite, cation exchange resin) materials.

Example 2

Detection of Adsorbed Cells

To the pellet of the experimental tests described in Example 1 was added an amount of 1 ml of B2P ColiQuik reagent (B2P limited, Auckland, New Zealand). The pellets were incubated at 37° C. and the time for the chromogen to change color from blue to pink was monitored. These incubation times are indicated in Table 1 below.

The materials exhibiting the highest level of attachment of the cells also, generally, result in very early change of color of the chromogen.

The non-visibility of the chromogen in the case of iron oxide and manganese oxide relates to the fact that the intense color of the material itself prevents the observation of a change in color of the chromogen.

TABLE 1

Efficacy of binding of *E. coli* to different adsorbent materials (Example 1), and detection test using the B2P ColiQuik reagent on attached cells (Example 2).

| Type of adsorbent material | % attached cells | B2P staining (hrs) |
|---|---|---|
| NONE | | |
| Controle | 0% | overnight |
| Controle | 0% | overnight |
| Controle | 0% | overnight |
| Controle | 0% | overnight |
| COLUMN MATERIALS | | |
| Hydroxyapaptite type 1 80 μm | 36% | 4.5 |
| Hydroxyapaptite type 1 80 μm | 39% | 4.8 |
| Hydroxyapaptite type 1 40 μm | 35% | 5.5 |
| Hydroxyapaptite type 2 40 μm | 35% | 5.0 |
| Macro-Prep Methyl HIC Support | 12% | 6.5 |
| Macro-Prep t-butyl HIC Support | 12% | 6.5 |
| Macro-prep CM-support | 36% | 5.0 |
| Macroperp High Q | 23% | 6.0 |
| Macro-prep DEAE Support | 7% | |
| Macro-prep High S support | 12% | 7.0 |
| Unosphere Cation Exchange support | 20% | |
| EXTRACTION *STREPTOCOCCI* | | |
| Invitrogen: Dynabeads ® Streptavidin 1 | 5% | Not visible |
| Invitrogen: Dynabeads ® Streptavidin 2 | 8% | Not visible |
| METAL OXIDES | | |
| Titanium oxide | 92% | 4-4.5 |
| Zirconium oxide | 87% | 4-4.5 |
| Hafnium oxide | 90% | 4-4.5 |
| Iron oxide | 75% | Not visible |
| Manganese oxide | 94% | Not visible |
| MISCELANEOUS | | |
| Sand | 0% | overnight |
| Perlite | 8% | 7.0 |

The invention claimed is:

1. A system for detecting micro-organisms in a liquid specimen, comprising:
   a device for concentrating micro-organisms from a liquid specimen, wherein the device comprises:
      a) a hyperbaric chamber for holding a liquid specimen comprising:
         a liquid inlet through which said liquid specimen can enter said hyperbaric chamber,
         a liquid outlet through which said liquid specimen can leave said hyperbaric chamber and adapted for sealably engaging with the liquid inlet of a filter housing, and
         means for pressurizing said hyperbaric chamber; and
      b) a filter housing comprising:
         a liquid inlet through which said liquid specimen can enter the filter housing and adapted for engaging with the liquid outlet of said hyperbaric chamber,
         a liquid outlet through which said liquid specimen can leave the filter housing, and
         a liquid-permeable bed of an adsorbent material housed in the filter housing between said liquid inlet and liquid outlet of said filter housing adsorbing micro-organisms through electrostatic interaction, wherein said adsorbent material has a positively charged surface, is in a granular form, having granules with a spherical particle size of between 5 μm and 1 mm; and comprises metal oxides and/or hydroxyapatite;
   whereby when:
      i) said hyperbaric chamber containing a liquid specimen is sealably engaged with said filter housing such that fluid communication between said hyperbaric chamber and said filter housing is allowed by means of a sealed passageway and
      ii) said hyperbaric chamber is pressurized, said liquid specimen is forced into the filter housing from said hyperbaric chamber and passes through said liquid-permeable bed of an adsorbent material before leaving via said liquid outlet;
   a kit for the detection of said micro-organisms by detecting enzymatic activity specific for said micro-organism comprising:

a chromogenic and/or fluorogenic substrate,
a liquid growth medium; and
optionally instructions for assembling, operating and disassembling the device, and/or detecting micro-organisms concentrated in said device by using said detection kit.

2. System according to claim 1, wherein said kit is for the detection of coliforms by detecting enzymatic activity of β-D-galactosidase and/or β-D-glucuronidase, respectively.

3. System according to claim 2, wherein said β-D-glucuronidase and/or β-D-galactosidase activity is detected by using a chromogenic or fluorogenic substrate selected from the group consisting of 4-methylumbelliferyl-β-D-glucuronide (MUG); ortho-nitrophenyl β-D-glucuronide (ONPG); para-nitrophenylβ-d-glucuronide (PNPG);β-naphthalamide-β-D-glucuronide; 6-bromo-2-naphthylβ-D-glucuronide; 5-bromo-4-chloro-3-indolyl β-D-glucuronide (BCIG or X-glucuronide); α-napthol-β-D-glucuronide; 4-methylumbelliferyl-β-D-galactopyranoside (MUGal), ortho-nitrophenyl-β-D-galactopyranoside (ONPGal); para nitrophenyl-β-D-galactopyranoside (PNPGal); 6-chloro-3-indolyl-β-D-galactopyranoside (Salmon-Gal), 5-bromo-4-chloro-3-indolyl-β-D-galactopyranoside (XGal);4-nitrophenyl 1-thio-β-D-galactopyranoside NPSGal), 6-bromo-2-naphthyl-β-d-galactopyranoside; 3,4-dinitrophenyl β-D-galactopyranoside (DNPGal), functional derivatives, and combinations thereof.

4. System according to claim 2, wherein said liquid growth medium comprises allolactose, isopropyl-β-D-thiogalactopyranoside (IPTG) and/or lactose.

5. A system according to claim 1, wherein said coliform micro-organism is *E. coli*.

6. A device for concentrating micro-organisms from a liquid wherein the device comprises:
a) a hyperbaric chamber for holding a liquid specimen comprising:
a liquid inlet through which said liquid specimen can enter said hyperbaric chamber,
a liquid outlet through which said liquid specimen can leave said hyperbaric chamber and adapted for sealably engaging with the liquid inlet of a filter housing, and
means for pressurizing said hyperbaric chamber; and
b)
a filter housing comprising:
a liquid inlet through which said liquid specimen can enter the filter housing and adapted for engaging with the liquid outlet of said hyperbaric chamber-,
a liquid outlet through which said liquid specimen can leave the filter housing, and
a liquid-permeable bed of an adsorbent material housed in the filter housing between said liquid inlet and liquid outlet of said filter housing adsorbing micro- organisms through electrostatic interaction, wherein said adsorbent material has a positively charged surface, is in a granular form, having granules with a spherical particle size of between 5 um and 1 mm; and comprises metal oxides and/or hydroxyapatite;
whereby when:
i) said hyperbaric chamber containing a liquid specimen is sealably engaged with said filter housing such that fluid communication between said hyperbaric chamber and said filter housing is allowed by means of a sealed passageway and
ii) said hyperbaric chamber is pressurized, said liquid specimen is forced into the filter housing from said hyperbaric chamber and passes through said liquid-permeable bed of an adsorbent material before leaving via said liquid outlet.

7. Device according to claim 6, wherein said filter housing is cylindrical and translucent at the position of the bed of an adsorbent material, and wherein said housing has an inner volume of between 1 and 10 ml.

8. Device according to claim 6, wherein said adsorbent material is selected from the group consisting of metal oxides on a support material.

9. Device according to claim 8, wherein said metal oxides are selected from the group consisting of zirconium oxide, titanium oxide, manganese oxide, iron oxide and hafnium oxide.

10. Device according to claim 6, wherein said adsorbent material comprises metal oxide nanoparticles on a support material, wherein said metal is selected from the group consisting of aluminium, calcium, cerium and zirconium.

11. Device according to claim 10, wherein said support material comprises hydroxyapatite.

12. Device according to claim 6, wherein said liquid is water.

13. Device according to claim 6, wherein said liquid inlet and said liquid outlet of said hyperbaric chamber are combined in a single port.

14. Device according to claim 6, wherein said micro-organism is *E. coli*.

15. A method for detecting micro-organisms in a liquid specimen, said method comprising the steps of:
a) -providing a system according to claim 1;
-loading a liquid specimen into said hyperbaric chamber;
-sealably engaging said hyperbaric chamber with the liquid inlet of said filter housing such that fluid communication between said hyperbaric chamber and said filter housing is allowed by means of a sealed passageway therebetween;
b) pressurizing said hyperbaric chamber loaded with said liquid specimen, thereby forcing said liquid specimen from said hyperbaric chamber into said filter housing whereby said liquid specimen passes through said liquid-permeable bed of the adsorbent material before leaving said filter housing via said liquid outlet and adsorbing onto the liquid-permeable bed of the adsorbent material said micro-organisms present in said liquid specimen;
c) continuing pressurizing said hyperbaric chamber until an effective amount of said liquid specimen has passed through said liquid-permeable bed of the adsorbent material;
d) incubating for an effective period of time said liquid-permeable bed of the adsorbent material with a liquid growth medium supplemented with a chromogenic and/or fluorogenic substrate in order to detect enzymatic activity of micro-organisms; and
e) monitoring the development of a chromogenic or fluorescent color to establish the presence or absence of micro-organisms adsorbed to adsorbent material, wherein the presence of micro-organisms adsorbed to said adsorbent material indicates the presence of micro-organisms in said liquid specimen.

16. Method according to claim 15, wherein said adsorbent material is selected from the group consisting of metal oxide on a support material.

17. Method according to claim 16, wherein said metal oxides are selected from the group consisting of zirconium oxide, titanium oxide, manganese oxide, iron oxide and hafnium oxide.

18. Method according to claim 15, wherein said adsorbent material comprises metal oxide nanoparticles on a support material, and wherein said metal is selected from the group consisting of aluminium, calcium, cerium, and zirconium.

19. Method according to claim 15, wherein said adsorbent material is hydroxyapatite.

20. Method according to claim 15, wherein said liquid is water.

21. Method according to claim 15, wherein said means for pressurizing said hyperbaric chamber is a syringe-type piston, or a deformable chamber wall allowing compression of the chamber and reduction of the chamber's inner volume.

22. Method according to claim 15, wherein said liquid growth medium and said chromogenic and/or fluorogenic substrate are for the detection of coliforms by detecting enzymatic activity of $\beta$-D-galactosidase and/or $\beta$-D-glucuronidase.

23. Method according claim 22, wherein said chromogenic and/or fluorogenic substrate is selected from the group consisting of 4-methylumbelliferyl-$\beta$-D-glucuronide (MUG); ortho-nitrophenyl $\beta$-D-glucuronide (ONPG); para-nitrophenyl $\beta$-d-glucuronide (PNPG); l3-naphthalamide- $\beta$-D-glucuronide; 6-bromo-2-naphthyl $\beta$-D-glucuronide; 5-bromo-4-chloro-3-indolyl $\beta$-D-glucuronide (BCIG or X-glucuronide); $\alpha$-napthol-$\beta$-D-glucuronide; 4-methylumbelliferyl-$\beta$-D-galactopyranoside (MUGal), ortho-nitrophenyl-$\beta$-D-galactopyranoside (ONPGal); para-nitrophenyl-$\beta$-D-galactopyranoside (PNPGal); 6-chloro-3-indolyl-$\beta$-D-galactopyranoside (Salmon-Gal), 5-bromo-4-chloro-3-indolyl $\beta$-D-galactopyranoside (X-Gal); 4-nitrophenyl 1-thio- $\beta$-D-galactopyranoside (NPSGal), 6-bromo-2-naphthyl-$\beta$-d-galactopyranoside; 3,4-dinitrophenyl $\beta$-D-galactopyranoside (DNPGal), functional derivatives, and combinations thereof.

24. Method according to claim 22, wherein said liquid growth medium comprises enzyme inducing agents such as allolactose, isopropyl-$\beta$-D-thiogalactopyranoside (IPTG) and/or lactose.

25. Method according to claim 22, wherein the presence of micro-organisms adsorbed to said adsorbent material is indicative of a potential contamination of said liquid specimen with faecal bacteria.

26. A method according to claim 15, wherein said micro-organism is *E. coli*.

* * * * *